US005393534A

United States Patent [19]
Cavanaugh et al.

[11] Patent Number: 5,393,534
[45] Date of Patent: Feb. 28, 1995

[54] LIVER-DERIVED TUMOR CELL GROWTH INHIBITOR

[75] Inventors: Philip G. Cavanaugh, Houston; Garth L. Nicolson, Kingwood, both of Tex.

[73] Assignee: Board of Regents, The University of Texas System, Austin, Tex.

[21] Appl. No.: 865,549

[22] Filed: Apr. 9, 1992

[51] Int. Cl.$^6$ .......................................... A61K 35/407
[52] U.S. Cl. ....................................... 424/553; 514/2; 514/21; 530/846
[58] Field of Search ................... 424/553; 514/2, 21; 530/846

[56] References Cited

PUBLICATIONS

Cavanaugh, Philip G., and Garth L. Nicolson, "Partial Purification of a Large Cell Lymphoma Growth Inhibitor from Liver," *Proceedings of the American Association for Cancer Research*, 32:55, 1991 Abstract No. 327.

Chapekar, Mrunal S., et al., "Growth Modulatory Effects of a Liver-Derived Growth Inhibitor, Transforming Growth Factor $\beta_1$, and Recombinant Tumor Necrosis Factor $\alpha$, in Normal and Neoplastic Cells," *Experimental Cell Research*, 185:247-257, 1989.

Chen, Thomas S., et al., "Fraction from Human and Rat Liver Which is Inhibitory for Proliferation of Liver Cells," *Cytobios*, 59:79-86, 1989.

Hamada, J., et al., "Analysis of Mouse Hepatic Endothelial Cell Growth-and Migration-Stimulating Factors for Liver-Colonizing Mouse Lymphoma Cell Lines," *Proceedings of the American Association for Cancer Research*, 32:62, 1991, Abstract No. 371.

Huggett, Anthony C., et al., "Characterization of a Hepatic Proliferation Inhibitor (HPI): Effect of HPI on the Growth of Normal Liver Cells-Comparison with Transforming Growth Factor Beta," *Journal of Cellular Biochemistry*, 35:305-314, 1987.

Kanda, Shigeru, et al., "A Study of Growth Regulatorrs of Renal Cortical Tubular Cells in the Rabbit Liver," *Kidney International*, 37:875-879, 1990.

Komatsu, K., et al., "Anchorage-Independent Cell Growth-Inhibiting Factor(s) from Normal Rat Liver and Ascites Hepatoma," *Cell Biology International Reports*, 10(10):813-820, 1986.

McMahon, James B., et al., "Purification and Properties of a Rat Liver Protein that Specifically Inhibits the Proliferation of Nonmalignant Epithelial Cells from Rat Liver," *Proceedings of the National Academy of Science, USA*.

Miyazaki, Kaoru, and Horio, Takekazu, "Growth Inhibitors: Molecular Diversity and Roles in Cell Proliferation," *In Vitro Cellular & Developmental Biology*, 25(10):866-872, 1989.

Nicolson, Garth L., "Differential Growth Properties of Metastatic Large-Cell Lymphoma Cells in Target Organ-Conditioned Medium," *Exp Cell Res*, 168:572-577, 1987.

Nicolson, Garth L, and Reuben Lotan, "Preventing Diversification of Malignant Tumor Cells During Therapy," *Clinical and Experimental Metastasis*, 4(4):231-235, 1986.

(List continued on next page.)

*Primary Examiner*—Douglas W. Robinson
*Assistant Examiner*—Jean C. Witz
*Attorney, Agent, or Firm*—Arnold, White & Durkee

[57] ABSTRACT

A factor has been purified from rat liver homogenate which displays preferential growth inhibitory effects on non-liver metastasizing tumor cells. The purification steps include heat treatment, ammonium sulfate precipitation, anion exchange chromatography, hydrophobic interaction chromatography, cation exchange chromatography, gel filtration chromatography, and preparative isoelectric focusing. The growth inhibitor obtained has an apparent $M_r$ of 38 kD to 40 kD and a pI of 9.1, it is not affected by reducing agents, and displays no biological TGF-b activity. This inhibitor exhibits less antiproliferative effect on liver metastasizing cells than on their non-liver metastasizing counterparts in two tumor systems: the murine RAW117 large cell lymphoma, and the human A375 melanoma.

14 Claims, 9 Drawing Sheets

PUBLICATIONS

Shirasuna, Kanemitsu, et al., "Growth Inhibition and Differentiation of Human Salivary Adenocarcinoma Cells by Medium Conditioned with Normal Human Fibroblasts," *Cancer Research*, 48:2819–2824, 1988.

Zhang, H., et al., "Characterization of Cell Surface Molecules Involved in Organ Preference of Tumor Metastasis with RAW117 System," *Proceedings of the American Association for Cancer Research*, 32:62, 1991 Abstract No. 372.

Reichelt, K. -L. et al., "Isolation of a Growth and Mitosis Inhibitory Peptide from Mouse Liver," *Virchows Archiv B Cell Pathology* 59:137–142, 1990.

Paulsen, J. E. et al., "The Peptide pyroGlu–Gln–Gly–Ser–Asn, Isolated from Mouse Liver, Inhibits Growth of Rat Hepatoma Cells in vitro," *Carcinogenesis* 12:207–210, 1991.

Paulsen, J. E. et al., "The Synthetic Hepatic Peptides Pyroglutamylglutamylglybylserylasparagine and Pyroglutamylglutamylglycylserylaspartic Acid Inhibit Growth of $MH_1C_1$ Rat Hepatoma Cells Transplanted into Buffalo Rats of Athymic Mice," *Cancer Research* 52:1218–1221, 1992.

Joshi, S. S. et al., "Enhanced and Proliferative Activity by Metastatic RAW117 Lymphoma Cells," *Clinical and Experimental Metastasis* 9:27–37, 1991.

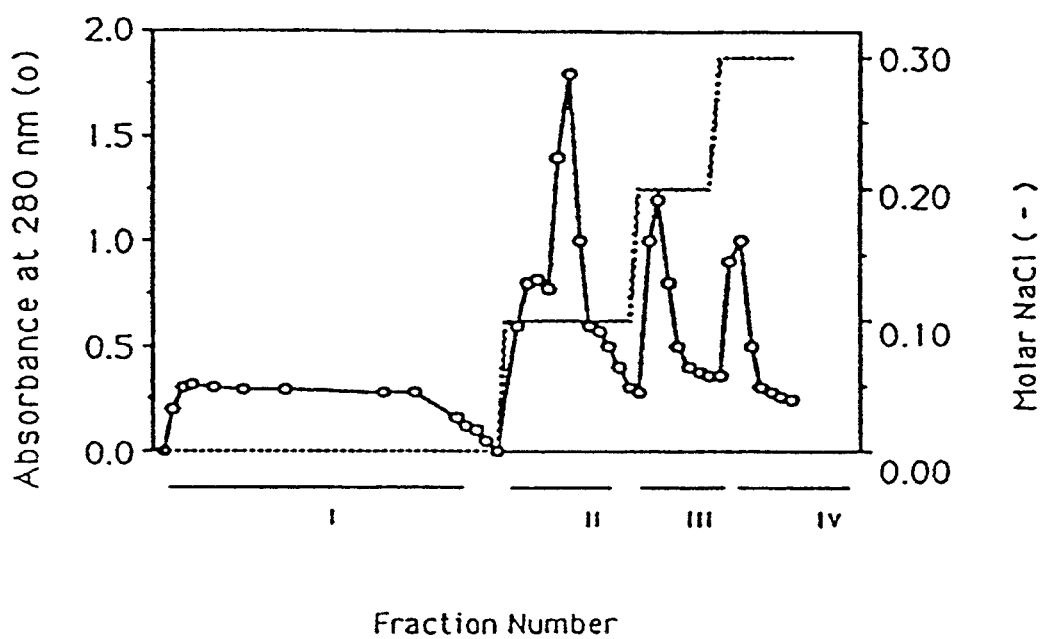
Fig. 2A1
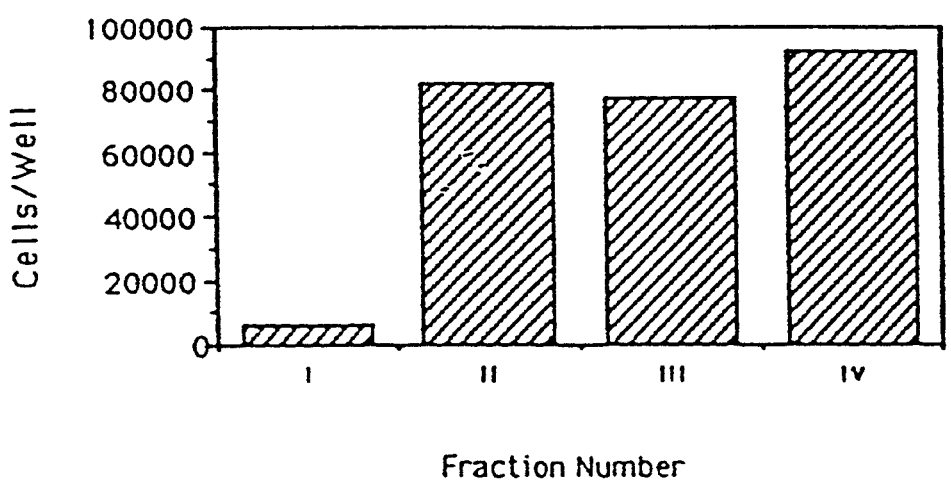
Fig. 2A2

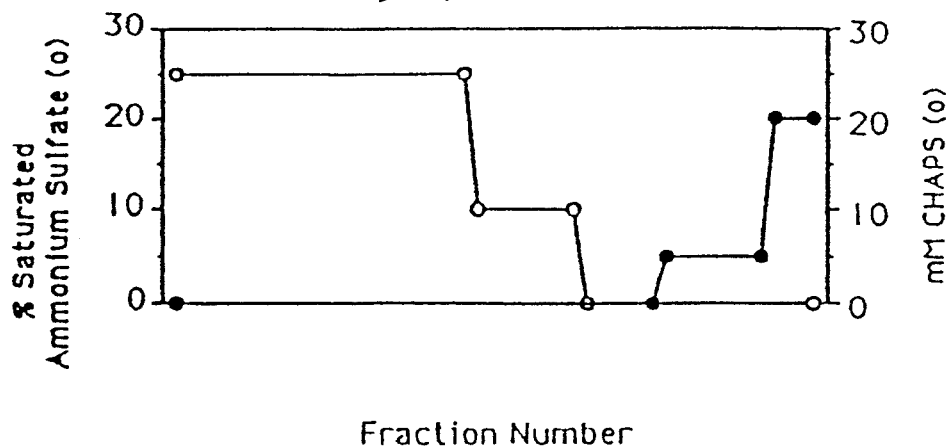
Fig. 2B1
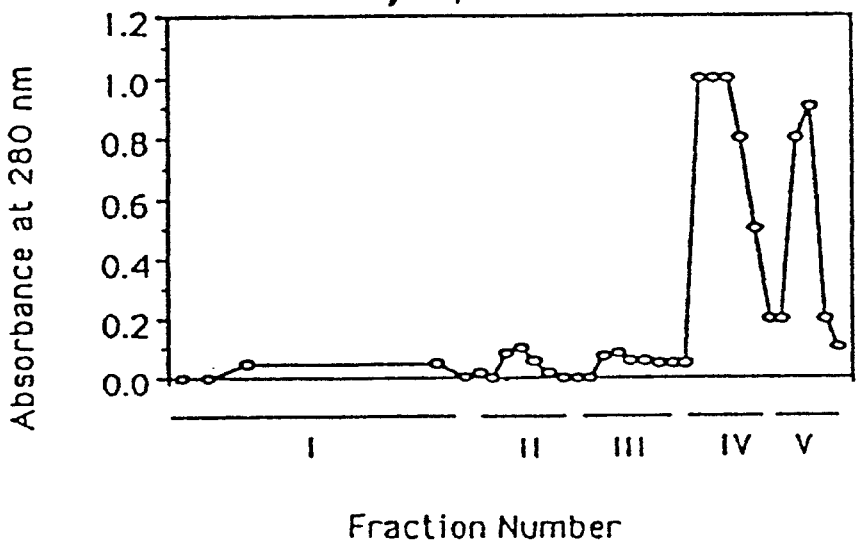
Fig. 2B2
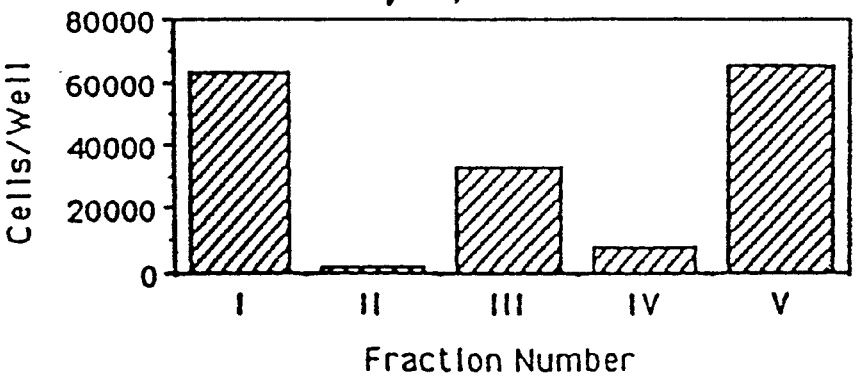
Fig. 2B3

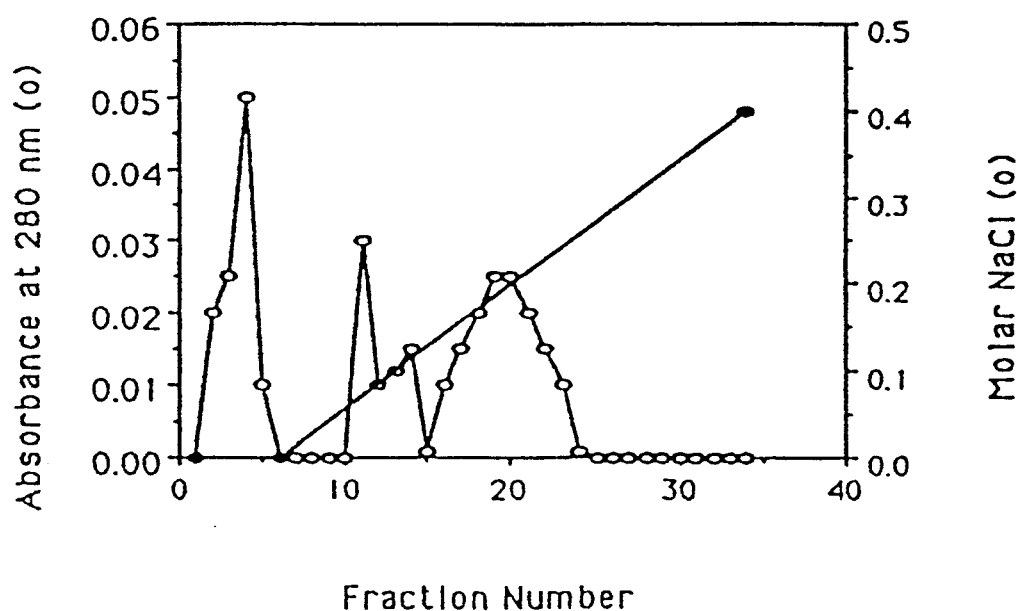
Fig. 2C1
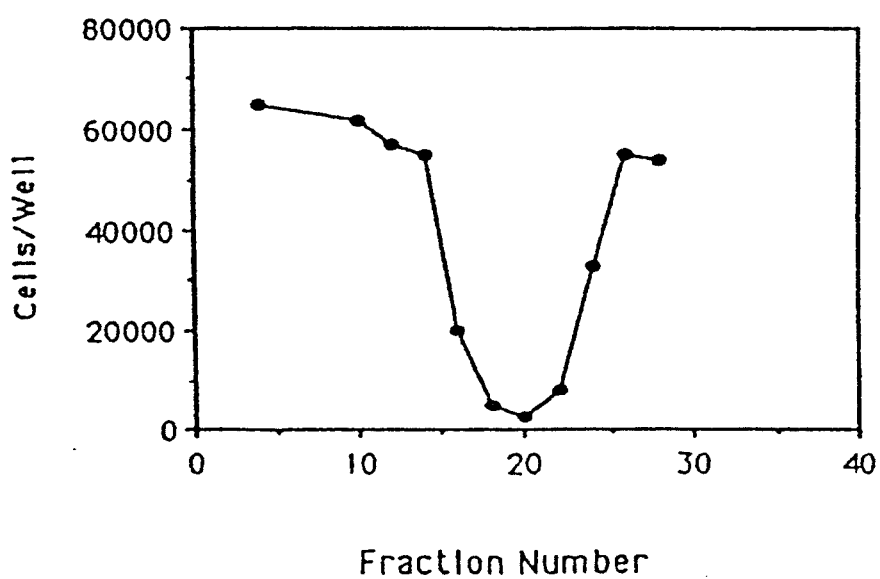
Fig. 2C2

$M_r (\times 10^{-3})$ 66, 45, 36, 29, 25, 20.1

Fig. 3

LIVER-DERIVED TUMOR CELL GROWTH INHIBITOR

BACKGROUND OF THE INVENTION

The government owns rights in the present invention pursuant to grant number 5R35-CA44352 (OIG) from the National Cancer Institute.

FIELD OF THE INVENTION

The present invention relates generally to the fields of cancer and cancer metastasis and to growth inhibitory factors. The invention is directed to the identification and purification of a growth inhibitory factor from liver tissues which inhibits tumor cell growth, and particularly, which differentially inhibits the growth of liver metastasizing and non-liver-metastasizing tumor cells. The invention is further directed to methods for inhibiting tumor metastasis to the liver and to methods for the identification of tumors which have increased metastatic potential with regard to the liver.

DESCRIPTION OF THE RELATED ART

The metastasis of a primary cancer to distinct sites within the body is a complex process involving a series of unique interactions between the tumorigenic cells, normal tissues and cells, and other, as yet undefined, factors. In this process the tumor cells invade distant tissues, where they survive and proliferate in the new environment and ultimately produce secondary lesions.

Metastasis of the primary tumor cells in such a manner leads to the emergence of unique tumor cell subpopulations that express altered malignant properties. This evidently presents a major obstacle to successful cancer treatment as the altered cells of the secondary lesion respond differently to therapeutic strategies. In model tumor systems, cytotoxic therapies that eliminate all but a few tumor cells seem to stimulate cell diversification to yield heterogeneous cell populations with divergent properties. Clinically the use of repeated cycles of cytotoxic therapies followed by intervening recovery period often results in the eventual emergence of highly resistant and increasingly malignant tumor cells.

Although certain primary cancers can sometimes be treated successfully using combinations of surgery, radiotherapy, chemotherapy and other procedures, these treatments often result in only the temporary control of cancer growth. The failure of combination and adjuvant therapies to eradicate malignant cells at metastatic sites is thought to be due to differences between the cellular properties of tumor cells found in primary and secondary lesions as well as to differences in the cells' anatomical environments and accessibilities to therapeutic agents.

Organ specific tumor metastasis may require the ability of metastatic cells to respond to target organ-associated growth factors or to avoid target organ situated growth inhibitors. Successful growth in the liver seems to be a property particular to liver metastasizing tumor cells. A correlation between the ability of tumor cells to grow in liver fragments in vitro and liver colonizing potential in vivo has been reported (Naito et al., 1987). It has also been shown that non liver metastasizing RAW117-P large cell lymphoma cells are growth inhibited by 3 and 6% v/v liver conditioned media but that the growth of their liver metastasizing RAW117-H10 counterparts is stimulated by the same material (Nicolson, 1987).

Various cellular proliferation promoters or inhibitors have described in recent times. For example, several growth inhibitors have been reported to be present within liver homogenates or liver derived cell lines (Table 1). However, the properties of such factors have only been defined in a limited sense and there remains relatively little documented information concerning the promotion or inhibition of normal or malignant cell growth in the liver. There is a particular lack of data relating to the possible relationship between any of these growth inhibitory factors and the colonization of the liver by metastasizing cancer cells.

TABLE I

Liver-Associated Cellular Proliferation Inhibitors

| Source | $M_r$ | Identification or other characteristics | Reference |
|---|---|---|---|
| Liver derived epithelial cell line | 56 kD<br>21 kD<br><14 kD<br><14 kD | N.S. | Mashima et al., 1988 |
| Rat liver homogenates | 17–19 kD | LDGI | Huggett et al., 1987; Chapekar et al., 1989 |
| Rat livers | 26 kD | non malignant epithelial cell proliferation inhibitor; pI = 4·65 | McMahon et al., 1982 |
| Human fetal liver | 120 kD | Arginase | Wu et al., 1989; 1989a |
| Mouse liver | <10 kD | N.S. | Paulsen et al., 1987 |
| | | Pentapeptide | Reichelt et al., 1990 |
| Rat liver extracts | 3·5–10 kD | inhibits EGF dependent colony formation of 3T3 cells | Komatsu et al., 1986 |
| Rabbit liver homogenates | 150–200 kD | inhibits renal cortical tubular cell growth | Kanda et al., 1990 |
| Murine hepatic endothelial cells | N.S. | inhibits 3T3 cell growth | Rosenbaum et al., 1989 |
| Liver homogenate fractions | 17–40 kD | N.S. | Chen et al., 1989 | kD; kilodaltons
N.S.; not specified
EGF; epidermal growth factor

The identification and characterization of tissue factors which inhibit tumor cell growth would be an important step towards a more complete understanding of the processes involved in metastatic invasion. The purification of such inhibitory factors could also lead to the development of new therapeutic anti-cancer strategies, addressed to inhibiting the metastasis of tumor cells, which are currently lacking in the art. The identification of growth inhibitors which exhibit differential activity towards metastatic and non-metastatic tumor cells would be particularly advantageous in the development of clinical diagnostic tests for potentially metastatic tumors.

SUMMARY OF THE INVENTION

The present invention seeks to overcome these and other drawbacks inherent in the prior art by the identification and purification of a factor, isolatable from liver cells, which inhibits tumor cell growth, and particularly, which exhibits differential inhibitory activity with respect to the growth of liver metastasizing and non-liver-metastasizing tumor cells. The invention further provides methods for inhibiting the metastasis of primary tumor cells to the liver and methods for the identification of tumors which exhibit increased liver-metastasizing potential.

The growth inhibitor of the present invention is functionally characterized as being a factor isolatable from liver cells which has the capability to inhibit cell growth. It is particularly characterized as having the capability to inhibit tumor cell growth, as exemplified by inhibiting the growth of, for example, the murine lymphoma cells, RAW117-P.

The liver-derived growth inhibitor disclosed herein is further characterized as having an isoelectric point of approximately 9.1; as possessing heat stability when treated for a period of time up to and including one hour at temperatures of between from ambient up to and including 65° C.; and as comprising one or more polypeptides, with molecular weights of approximately 38 kD to 40 kD, as determined by gel filtration chromatography and SDS/PAGE analyses performed as described hereinbelow. It is, of course, generally known in the art that molecular weight determinations made using such methods can vary with differing conditions, for example, see Capaldi et al. (1977) which refers to discrepancies between SDS/PAGE methods. It will therefore be appreciated that under differing conditions, the molecular weight assignments quoted above may vary.

As used herein, the term "having the capability to inhibit cellular proliferation" is intended to refer to the capacity of a given composition to inhibit cellular growth or proliferation to any detectable degree, i.e. to reduce growth or proliferation below the levels observed in the absence of the composition. In the broadest sense, it is contemplated that any cell type may be used to analyze the effects of the growth inhibitors, such as, non-transformed liver cells maintained in culture, or indeed, cultured cells from any other tissues. Such cells include, for example, normal hepatocytes, liver sinusoidal endothelial cells, liver-derived fibroblasts, or other normal tissue fibroblasts such as normal rat kidney fibroblasts (NRK cells), or normal endothelial cells from various tissues, including lung and brain endothelial cells.

In preferred embodiments, the use of tumor cells in assays of growth inhibitory factors is contemplated. Virtually any type of tumor cell from any source will be suitable, such as, for example, established tumor cell lines of any origin, including, but clearly not limited to, the murine large-cell lymphoma line RAW117-P, the human melanoma line A375P, and the rat mammary adenocarcinoma cell line 13762NF. It is further contemplated that one could also use cultured tumor cells newly isolated from any animal or human tumor.

A further and important property of the growth factor of the present invention is the ability to inhibit the growth of liver metastasizing and non-liver-metastasizing tumor cells differentially. Such properties can be examined using non-metastatic parental tumor cell lines and their metastatic sublines in parallel cellular proliferation assays. In preferred embodiments, the use of parental and metastatic sublines such as RAW117-P and RAW117H10; A375P and A375Li; and 13762NF and its metastasizing variant MTLn3, is contemplated. However, it will be understood by the skilled artisan, in light of the present disclosure, that any combination of cell lines and variants known in the art may be suitable for use in such embodiments.

Various methods are contemplated to be of use in determining the inhibition of cell growth or proliferation, i.e., for use in assaying the activity of the growth inhibitory factors. Such assays include, but are not limited to, in vitro assays such as the uptake and elution of crystal violet dye; the MTT assay for staining and quantitation of live cells in a culture dish; or the incorporation of radioactive, or non-radioactive labels, such as $^3$H-thymidine, or bromodeoxy uridine, respectively, into TCA-precipitable cellular DNA. In certain embodiments, the use of assays based upon the uptake and elution of crystal violet dye is particularly preferred as such assays have been found to be relatively straightforward and inexpensive, to give reliable results, and to avoid the use of radiochemicals.

Further aspects of the present invention concern the purification, and in particular embodiments, the substantial purification, of a growth inhibitor. The term "purified growth inhibitor" as used herein, is intended to refer to a growth inhibitor composition, isolatable from liver cells, wherein the growth inhibitor is purified to any degree relative to its naturally-obtainable state, i.e., in this case, relative to its purity within a liver extract. Where the term "substantially purified" is used, it refers to a growth inhibitor composition, isolatable from liver cells, which has been subjected to fractionation to remove various non-growth inhibitor components, and which composition substantially retains its growth inhibitory activity.

Various methods for quantifying the degree of purification of the inhibitor will be known to those of skill in the art in light of the present disclosure. These include, for example, determining the specific activity of an inhibitory fraction, or assessing the number of polypeptides within a fraction by SDS/PAGE analysis. A preferred method for assessing the purity of an inhibitory fraction is to calculate the specific activity of the fraction, to compare it to the specific activity of the initial liver cell extract, and to thus calculate the degree of purity, herein assessed by a "−fold purification number".

The actual units used to represent the amount inhibitory activity will, of course, be dependent upon the particular assay technique chosen to follow the purification. As discussed above, the present inventors prefer to use an assay based upon the uptake and elution of crystal violet dye. One unit of activity in the assay used herein is defined as the inhibitory activity required to cause the reduction of the number of cells/well in test wells to 30% of that seen in negative control wells. However, using other assays, the definition of a unit of activity would naturally vary. It may be assessed as, for example, the inhibitory activity required to reduce the uptake of $^3$H-thymidine (or bromodeoxy uridine) into TCA-precipitable cellular DNA in test assays to a defined % less than that seen in negative control assays.

As is generally known in the art, to determine the specific activity, one would calculate the number of units of activity per milligram of total protein. In the purification procedure, the specific activity of the starting material, i.e., of the liver cell extract, would represent the specific activity of the inhibitor in its natural state. At each step, one would expect the specific activity of the inhibitor to increase above this value, as it is purified relative to its natural state. In preferred embodiments, it is contemplated that one would assess the degree of purity of a given inhibitory fraction by comparing its specific activity to the specific activity of the starting material, and representing this as X-fold purification. The use of "fold purification" is advantageous as the purity of an inhibitory fraction can thus be compared to another despite any differences which may exist in the actual units of activity or specific activity.

It is contemplated that the growth inhibitor of the present invention be purified to between about 1.4-fold and about 100-fold, and preferably, of between about 10-fold and about 100-fold, and even more preferably, to about 100-fold, relative to its natural state.

To prepare a substantially purified growth inhibitor in accordance with the present invention one would first prepare an extract from liver cells, for example, a homogenate from the liver of an animal, such as from rat, ox, pig, or even human liver. Alternatively, one may wish to employ conditioned media obtained from liver cells in culture as the source of starting material. Naturally, in choosing this purification route, one would firstly perform a routine initial assay to confirm the presence of similar inhibitory activity in the conditioned media. One would then subject the extract from the liver cells to a series of fractionation procedures, the number of fractionation steps employed being dependent on the degree of purification desired and the intended use of the resultant growth inhibitor, for example, clinical, analytical, antigenic, etc.

The preferred purification method disclosed hereinbelow contains several steps and represents the best mode presently known by the inventors to prepare a substantially purified growth inhibitor. This method is currently preferred as it results in the substantial purification of the growth inhibitor, as assessed by SDS/PAGE and silver stain analysis, in yields sufficient for further characterization and use. This preferred mode of growth inhibitor purification involves the execution of certain purification steps in the order described hereinbelow. However, as is generally known in the art, it is believed that the order of conducting the various purification steps may be changed, or that certain steps may be omitted, and still result in a suitable method for the preparation of a substantially purified growth inhibitor.

During purification process, one would naturally wish to conduct assays to detect the growth inhibitory activity at various stages. To carry out the best mode purification procedure, one would firstly obtain an extract of animal liver, such as a rat liver homogenate. This may be prepared, for example, by homogenizing a number of rat livers in a high speed blender, with a suitable buffer, preferably containing protease inhibitors, such as 25 mM HEPES, pH 7.5, 1 mM PMSF, 1 mM TPCK, 2 mM EDTA. The particulate material should then be removed from the extract, for example by centrifugation, or preferably, by centrifugation following two freeze-thaw cycles.

The resulting supernatant should next be heat treated, for example, by exposure to 65° C. for 1 hour, and again centrifuged to remove any heat sensitive pelletable material. One would then subject the supernatant to ammonium sulfate precipitation, preferably by creating a 70% saturated solution by the addition of solid ammonium sulfate. The resulting suspension should be stirred, preferably at 4° C., for a period of time sufficient to allow the precipitation of the growth inhibitor from solution, such as from 30 to 60 minutes. The suspension would be centrifuged and the precipitate resuspended in a suitable buffer, such as 25 mM HEPES pH 7.5, and traces of ammonium sulphate removed, for example, by dialyzing against the same buffer.

This partially purified dialysate could then be subjected to a series of column chromatography steps, each of which adds a further degree of purity to the inhibitor. Firstly, one would subject the material to ion exchange chromatography using, for example, a QAE-Sepharose or MonoQ (Pharmacia) column equilibrated with a low salt containing buffer, such as 25 mM HEPES, pH 7.5. The column would be washed with the same buffer to remove non-binding species which would be collected.

One would next add ammonium sulfate to this fraction to make a saturated solution on the order of 25% saturation, apply this material to an octyl-agarose column previously equilibrated in the same ammonium sulfate-containing buffer, and wash the column with the same solution. Bound components could be eluted in a stepwise manner, firstly with batches of the buffer containing decreasing ammonium sulfate concentrations, and then with the same buffer containing increasing concentrations of a detergent, such as the zwitterionic detergent CHAPS. Aliquots of the batch fractions should again be tested-for growth inhibitory activity, when it is anticipated that the activity would be found in the 10% saturated ammonium sulfate eluting fraction.

This fraction should be dialyzed against a low salt containing buffer, such as 25 mM potassium phosphate, pH 6.0, and applied to a CM-sepharose column equilibrated in the same buffer. Bound components could be eluted using an increasing salt gradient, such as the above buffer containing 0.0–0.4M NaCl , when it is anticipated that the activity would be found in the 0.15–0.20M NaCl eluting fraction. The active pool obtained in this manner should be concentrated to a smaller volume, on the order of approximately 1 ml, using an appropriate concentration technique, such as by employing a Amicon YM-2 filter.

The resulting concentrated fraction would then be applied to a gel filtration column, for example, a Bio-gel P 200 column, equilibrated with a buffer such as 25 mM HEPES, preferably containing a low concentration of salt, in the order of 0.2M NaCl. Aliquots of these final column fractions should be tested for growth inhibitory activity, and it is anticipated that the activity would be found in the fractions eluting with a molecular weight corresponding to approximately 38 kD to 40 kD.

A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule. Techniques such as these would also, of course, be appropriate for the production of a growth inhibitor in accordance with the present invention.

The first step in such cloning procedures is the screening of an appropriate DNA library, such as, in the present case, a liver-derived library. The screening procedure may be an expression screening protocol employing antibodies directed against the protein, or activity assays. Alternatively, screening may be based on the hybridization of oligonucleotide probes, designed from a consideration of portions of the amino acid sequence of the protein, or from the DNA sequences of genes encoding related proteins. After identifying an appropriate DNA molecule, it may be inserted into any one of the many vectors currently known in the art and transferred to a prokaryotic or eukaryotic host cell where it will direct the expression and production of the so-called recombinant version of the protein.

It is envisioned that growth inhibitors prepared in accordance with the present invention may be advantageously used in a number of different embodiments. Importantly, such novel inhibitors will have clinical utility in the treatment of cancer. In preferred embodiments, they will be useful in anti-cancer strategies addressed to inhibiting the metastasis of tumor cells, and in particular, of inhibiting the metastasis of tumor cells to the liver. Such treatment regimens are particularly important as therapeutic methods addressed to inhibiting metastasis are currently lacking in the art. In that the novel growth inhibitors exhibit differential activity towards certain metastatic tumor cells and their non-metastatic counterparts, they will have further utility in clinical diagnostic tests to identify potentially metastatic tumors, and thus to allow therapy to be planned accordingly.

As mentioned above, although preferred for use in certain embodiments, there is no general requirement that the growth inhibitors always be provided in their most purified state. Indeed, it is contemplated that less substantially purified growth inhibitors, which are nonetheless enriched in growth inhibitory activity relative to the natural state, will have utility in certain embodiments. These include, for example, the large scale screening for inhibitory activity against panels of metastatic and non-metastatic tumor cells, or in determining the metastatic potential of tumor cells obtained from a biopsy sample. Partially purified growth inhibitor fractions for use in such embodiments may be obtained by subjecting a liver cell extract to one or a combination of the steps described above.

In further embodiments, the invention provides methods for the identification of tumors which exhibit increased liver-metastasizing potential. To perform such a diagnostic method, one would firstly obtain cells from the tumor, as is routinely performed in the art, by conducting a tissue biopsy, and then contact the tumor cells with a growth inhibitor prepared in accordance with the present invention. One would determine the level of cell growth or proliferation in the presence of the inhibitor and compare it to the control growth levels observed in the absence of the inhibitor. Cells which maintain the ability to proliferate substantially in the presence of the inhibitor would be identified as cells having increased metastatic potential with respect to the liver. Treatment regimens could then be planned accordingly taking into consideration the newly defined properties of the tumor cells.

To treat cancer, or more precisely, to inhibit the metastasis of tumor cells, using the growth inhibitor of the present invention, one would simply administer a therapeutic amount of the growth inhibitor to an animal with cancer. This can be achieved by any of the methods currently used in the art, such as parenteral administration or administration of the inhibitor in an encapsulated form. It is contemplated that this treatment could be performed either subsequent to, or simultaneously with, the surgical removal of a tumor or tumors from an animal. It is further contemplated that the administration of the growth inhibitor could be advantageously combined with other anti-cancer therapies, such as in conjunction with radiotherapy or chemotherapy.

In such cancer treatment embodiments, it is contemplated that the novel growth inhibitor may be administered alone or in combination with pharmaceutically acceptable carriers, in either single or multiple doses. For parenteral administration, including intravenous, intramuscular and subcutaneous injection, solutions of the inhibitor in various oils, emulsions, or aqueous sterile buffers may be employed. The precise compositions and use of such pharmaceutical carriers will be known to those of skill in the art in light of the present disclosure.

For direct delivery of the inhibitor to tissues, it is contemplated that the inhibitor may also be given in a liposome-encapsulated form. Such techniques are known to increase the efficacy and significantly prolong the half-life of administered compounds, and particularly, compounds of lower molecular weight. Liposome encapsulation can be accomplished in a number of manners, for example, as described by Fidler et al. (1976).

BRIEF DESCRIPTION OF THE DRAWINGS

FIGS. 2A1, 2A2, 2B1, 2B2, and 2B3, 2C1, 2C2 and 2D. Chromatograms obtained from the purification of the liver derived growth inhibitor. A: anion exchange of the ammonium sulfate precipitate on QAE sepharose. B: hydrophobic interaction separation of the pool from A on octyl agarose. C: cation exchange chromatography of the pool from B on CM-sepharose. D: gel filtration separation of the pool from C on Bio-gel P-200.

FIG. 3. SDS-PAGE analysis of the active growth inhibitory material pool from FIG. 2D. Samples were separated on a 10% acrylamide gel run according to Laemmli (1970) and detected by silver stain. Lane 1, molecular weight standards; lane 3, 2 μg reduced growth inhibitor; lane 7, 2 μg non-reduced inhibitor. Standards and molecular weights: bovine serum albumin ($M_r \sim 66,000$), ovalbumin ($M_r \sim 45,000$), glyceraldehyde-3-phosphate dehydrogenase ($M_r \sim 36,000$), carbonic anhydrase ($M_r \sim 29,000$), trypsinogen ($M_r \sim 24,000$), and soybean trypsin inhibitor ($M_r \sim 20,100$).

DETAILED DESCRIPTION OF THE PREFERRED EMBODIMENTS

Figure 1A:
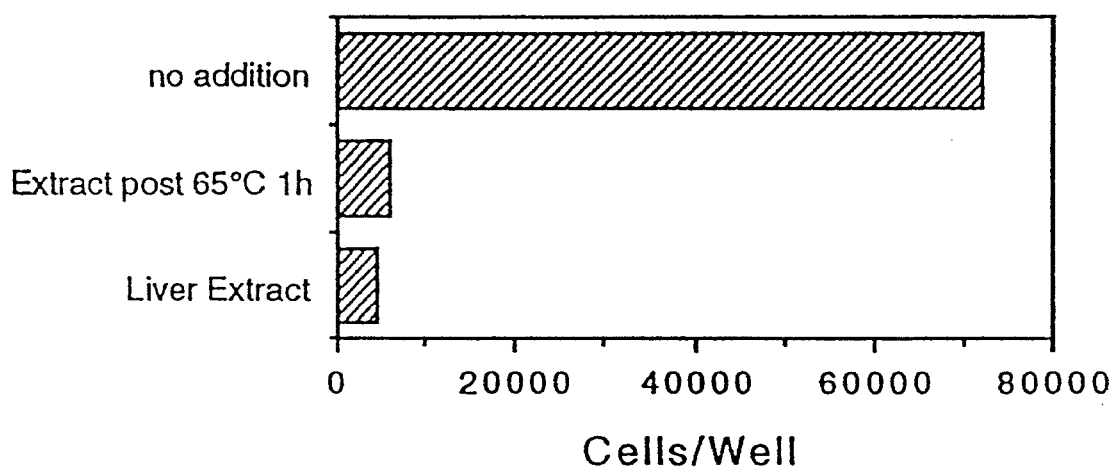
FIGS. 1A and 1B. A: heat stability of crude liver growth inhibitory activity. The initial 100,000×g supernatant was exposed to 65° C. for 1 hour and tested on RAW117P cells as described in Example I. B: solubility of the inhibitor in increasing ammonium sulfate, performed as described in Example I. For A and B, bars represent the mean of duplicate wells.

Many, if not all, naturally occurring and induced neoplasms are thought to develop from single cells. Although well-advanced tumors still retain evidence of such clonal origin, malignant neoplasms are composed of diverse cell populations that are heterogeneous for a variety of properties, including metastatic potential and therapeutic sensitivity. Such heterogeneity also extends to tumoricidal macrophage sensitivity, once considered to be expressed homogeneously among malignant cells. Thus, malignant neoplasms evolve during their life history to form tumors with cellular diversity and altered properties. In addition, such heterogeneous tumor cell populations probably undergo extensive in vivo selection, resulting in tumor cells that possess competitive advantages over neighboring treatment-sensitive tumor cells and, ultimately, in the emergence of unique tumor cell subpopulations with increasingly diverse properties and enhance autonomy, survival, growth and malignant characteristics.

Where the metastasis of a primary cancer to distant sites is concerned, the ability to tolerate cytostatic conditions in the target organ for metastasis may be a tumor cell property required for successful tumor formation at that site. The liver seems to be a source of many different cellular proliferation inhibitors. It has been therefore been reasoned that in studying the ability of tumor cells to colonize the liver, an investigation of tumor cell growth inhibitor avoidance may be important.

In support of this, Hart (1982) found that liver metastasizing murine M5076 reticulum sarcoma cells were more resistant to the thymidine uptake inhibiting activity of a liver extract than were non-liver metastasizing murine B16 melanoma cells. Later studies have indicated that liver metastasizing cells are more tolerant of the liver environment (Naito et. al., 1987) or of liver conditioned media (Nicolson, 1987) than are non-liver metastasizing cells.

The present study was undertaken to investigate the possibility that a differential response to hepatic growth inhibitors occurs in defined liver metastasizing tumor systems, to purify and characterize the responsible components, and to explore the relationship between such inhibitory factors and the establishment of metastatic tumors in the liver.

The purification of the liver-derived growth inhibitors disclosed herein was achieved using an assay based upon the inhibition of proliferation of non-liver metastasizing tumor cells as the indicator of activity. A tumor cell proliferation inhibitor was isolated from liver homogenates and subsequently purified to apparent homogeneity using a five step purification process. This growth inhibitory protein was found to be heat stable, to possess an apparent $M_r$ of approximately 38 to 40 kD, and to have a pI of approximately 9.1–9.2.

A comparison of these properties with those of previously described liver-derived growth inhibitors, for example, see Table I, reveals this inhibitor to be a novel hepatic factor. Shirasuna et. al. (1988) have described a factor from the conditioned media of normal human lip mucosa fibroblasts which reportedly inhibits the growth of human salivary adenocarcinoma cells. This factor is said to be relatively heat stable and to possess a molecular weight of approximately 40,000 as assessed by gel filtration using a Superose 12 (Pharmacia) column. However, no further characteristics or properties attributale to this mucosal fibroblast factor have subsequently been reported in the scientific literature.

It is believed that the growth inhibitors of the present invention will have utility in a variety of embodiments, particularly important uses being in the treatment of cancer. In preferred embodiments, the inhibitors will be useful in anti-cancer strategies addressed to inhibiting the metastasis of tumor cells, and in particular, of inhibiting the metastasis of tumor cells to the liver. This represents an important development in the art, as therapeutic methods addressed to inhibiting metastasis are not currently particularly successful.

As the novel growth inhibitors disclosed herein exhibit differential activity towards certain metastatic tumor cells and their non-metastatic counterparts, this opens up further avenues of clinical investigation and diagnosis. The inhibitor has great potential for use in clinical diagnostic tests to identify potentially metastatic tumors, so providing further information in light of which the most appropriate therapeutic strategy could be implemented.

In such methods for treating cancer, the inhibitor may be administered parenterally, for example, employing solutions of the growth inhibitor in sesame or peanut oil, aqueous propylene glycol, or in sterile aqueous solutions. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice.

However, those of skill in the art should, in light of the present disclosure, appreciate that many changes can be made in the specific embodiments which are disclosed and still obtain a like or similar result without departing from the spirit and scope of the invention.

EXAMPLE I

PURIFICATION OF A LIVER-DERIVED TUMOR CELL GROWTH INHIBITOR

A. MATERIALS AND METHODS

1. Materials

Bio-gel P-200, the Rotofor instrument and Coomasie blue protein reagent were obtained from Bio-Rad (Richmond, Calif.). Tissue culture media, fetal bovine serum (FBS) and reagents were obtained from Gibco (Grand Island, N.Y.). All other materials were obtained from Sigma chemical (St. Louis, Mo.).

2. Cell lines

The murine large-cell lymphoma line RAW117 was derived from BALB/c splenocytes infected with Abelson leukemia virus. The parental cell line (RAW117-P) possessed poor metastatic potential in syngeneic mice. A variant subline (RAW117-H10) selected ten-times for liver colonization-was highly metastatic after i.v. or s.c. injection (Brunson and Nicolson, 1978). These cell lines were grown as suspension cultures in plastic Petri dishes with 5 mM HEPES (N-[2-Hydroxethyl] piperazine-N'-[2-ethanesulfonic acid]) buffered DME (pH 7.5) supplemented with 5% FBS and 2.2 mM D-glucose. The human A375P melanoma parental line was obtained from Dr. I. J. Fidler of the University of Texas M. D. Anderson Cancer Center. The A375Li line was selected from a liver metastasis produced in nude mice by the A75P line. The A375 lines were maintained in DME:F12 (1:1, v:v) containing 5% FBS. All cells were of low passage recovered from frozen stocks and were found to be free of Mycoplasma spp. contamination with the Gen-Probe rapid detection system (Fischer, Tustin, Calif.).

3. Growth inhibition assays

Aliquots of fractions to be tested were dialyzed against 25 mM HEPES, pH 7.5, made 1× in media components by the addition of 1/9 volume 10×MEM, and were filter sterilized. Cells were plated at 2,000 cells/well into 96 well plates in 100 μl of 25 mM HEPES buffered (pH 7.5) high glucose DMEM containing 2% FBS. Prepared fractions were added in quadruplicate at 10% v/v and cultures were incubated for 5 days in a humidified 37° C., 5% $CO_2$ environment. Cell number was then quantitated using a model ZM Coulter Counter. Adherent cell numbers were quantitated using a crystal violet staining procedure (Keung et. al., 1989), where $A_{590}$ correlates linearly with cell number up to 40,000 cells/well. All results were compared to those obtained using dialyzed control solutions.

One unit of inhibitory activity is herein defined as causing the reduction the number of cells/well in test wells to 30% of that seen in negative control wells. To obtain a value for the specific activity at each step of the purification procedure, various amounts of each fraction were tested and a dose response curve for each fraction was generated. The specific activity, i.e., the units of inhibitory activity per milligram of protein (units/mg), was then interpolated from the dose response curve.

4. SDS/PAGE

Polyacrylamide gel electrophoresis in the presence of sodium dodecyl sulphate (SDS/PAGE) was performed according to Laemmli (1960).

5. Protein assays

Protein concentrations were determined using the Bio-Rad Coomasie blue plus dye binding assay.

B. RESULTS

RAW117P cells were used as target cells in all assays performed throughout the purification. Twenty rat livers were homogenized using a high speed blender in 400 ml 25 mM HEPES, pH 7.5 containing 1 mM PMSF, 1 mM TPCK, and 2 mM EDTA. The homogenate was exposed to two freeze-thaw cycles and centrifuged at 100,000×g for 1 hour.

The heat stability of this liver homogenate was first analyzed. The liver extract was placed in a 65° C. water bath for 1 hour. The homogenate was then centrifuged at 5,000× g for 30 minutes and the growth inhibitory activity of the resulting supernatant was determined. It was found that the proliferation inhibitory activity for RAW-117P cells contained in a liver homogenate was not affected by high temperatures of up to and including 65° C. (FIG. 1A). Heat exposure caused a precipitate to form in the homogenate, which did not contain growth inhibitory activity and which could was removed by the centrifugation step. Such a heat treatment protocol was therefore chosen as the initial step in the purification procedure.

To recover the activity from the heat-treated supernatant ammonium sulphate precipitation was investigated. The extract was made 50% saturated in ammonium sulfate by the addition of solid ammonium sulfate, stirred for 30–60 minutes at 4° C. and centrifuged at 5,000×g for 20–30 minutes. The resulting precipitate was suspended in 25 mM HEPES, pH 7.5. The supernatant from this step was then made 60% saturated in ammonium sulfate, stirred and centrifuged as above. The process was repeated at 70% and 80% ammonium sulfate saturations. Aliquots of the resulting precipitates and the final supernatant were tested for growth inhibitory activity.

Figure 1B:
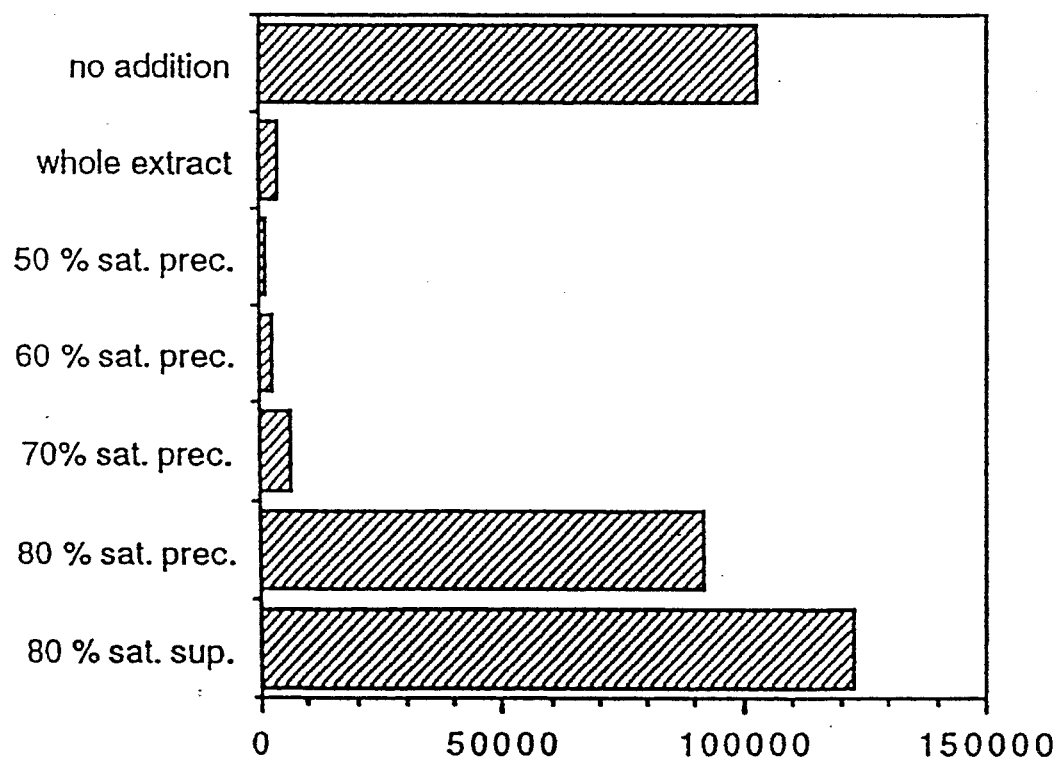

From an analysis of the fractions obtained in the various ammonium sulphate precipitation steps, it was determined that all of the activity could be precipitated from the heat treated supernatant by making it 70% saturated in ammonium sulfate (FIG. 1B), which was therefore employed as the second step in the purification.

The precipitate from the 70% ammonium sulfate cut was resuspended in 25 mM HEPES pH 7.5, dialyzed against the same buffer, and subjected to further purification. The dialysate was applied to a 2.5×10 cm QAE-Sepharose column equilibrated with 25 mM HEPES, pH 7.5. Bound components were eluted stepwise with equilibration buffer containing 0.1, 0.2 and 0.3M NaCl and resulting batch fractions were tested for growth inhibitory activity. It was found that this resolubilized growth inhibitor would not adhere to QAE-sepharose at a pH of 7.5 (FIG. 2a) or pH 8.5, indicating that it possessed a high iso-electric point. Thus, passage through QAE-sepharose resulted in significant purification (FIG. 2a).

The unbound fraction from the QAE-sepharose step was then made 25% saturated in ammonium sulfate and applied to a 1×10 cm octyl-agarose column previously equilibrated in 25 mM HEPES, pH 7.5 containing 25% saturated ammonium sulfate. The growth inhibitory activity was found to bind to the octyl-agarose under these conditions. Bound components were eluted stepwise, first with 25 mM HEPES, pH 7.5 containing decreasing ammonium sulfate concentrations. The major source of growth inhibitory activity eluted from this column when the ammonium sulfate concentration was reduced to 10% saturation (FIG. 2b). The protein concentration of this fraction was again reduced, resulting in a high specific growth inhibitory activity.

The octyl-agarose column was then washed with the above buffer containing increasing concentrations of the zwitterionic detergent CHAPS ((3-[3-Cholidamidopropyl)-dimethylammonio]1-propanesulfonate). It was found that most of the protein had adhered strongly to the column and could be eluted only in the presence of the CHAPS detergent. This emphasizes that significant purification was achieved at this stage.

The fraction obtained from octyl-agarose column was dialyzed against 25 mM potassium phosphate, pH 6.0, and applied to a 1×5 cm CM-sepharose column equilibrated in this buffer. Bound components were eluted with 150 ml of a 0–0.4M NaCl in 25 mM potassium phosphate, pH 6.0, using a flow rate of 0.5 ml/minute. Fractions (5.0 ml) were collected tested for growth inhibitory activity. It was determined that the growth inhibitor bound to CM-sepharose at pH 6.0, and could be recovered from this column by using 0.15–0.20M NaCl (FIG. 2c).

Figure 2D:
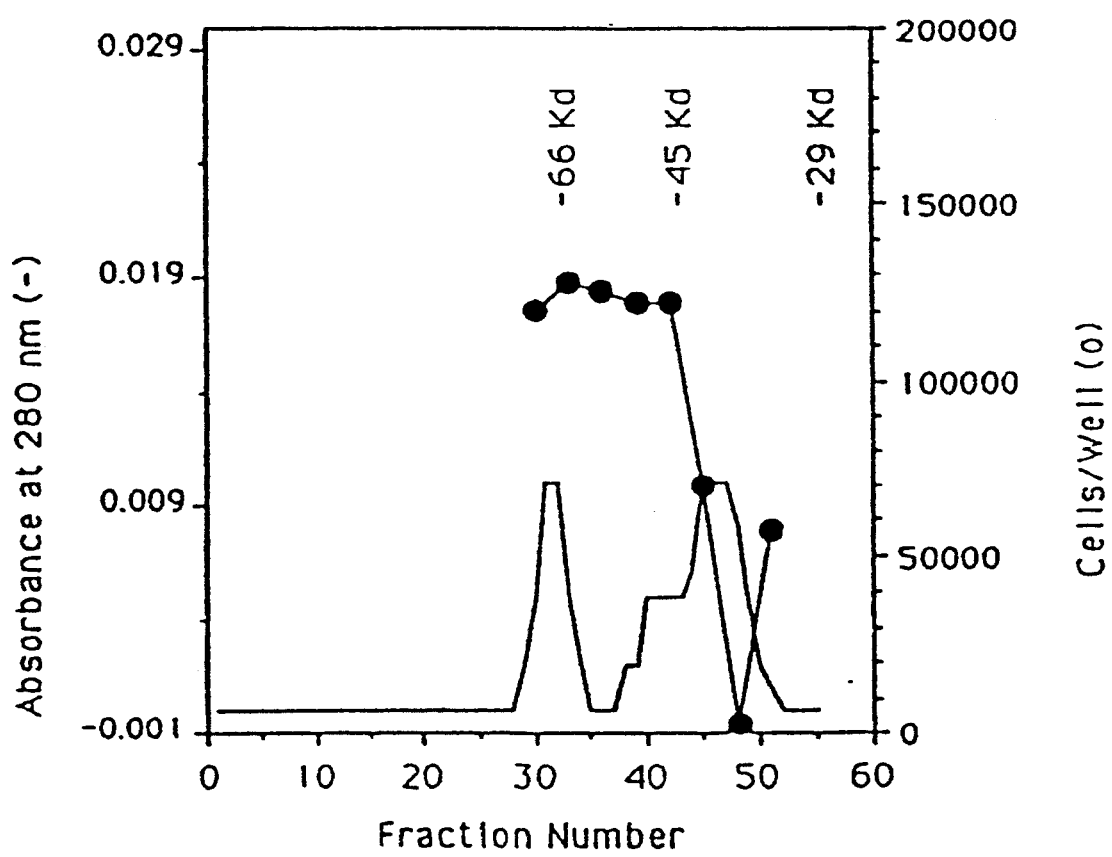

The active pool from the CM-sepharose step was concentrated to 1 ml using an Amicon YM-2 filter and applied to a 2.5×50 cm Bio-gel P 200 column equilibrated with 25 mM HEPES, 0.2M NaCl. This gel filtration step was conducted using a flow rate of 12 ml/hour and 2 ml fractions were collected and tested for growth inhibitory activity. The growth inhibitory activity was found to elute with an $M_r$ of ~40,000 (FIG. 2d).

Using the above-described purification procedure the growth inhibitor was purified from a specific activity of approximately 48 units/mg protein in the initial homogenate to approximately 5,000 units/mg protein after the gel filtration chromatography step (Table II). To obtain a value for the specific activity at each step in the procedure, as summarised in Table II, various amounts of each fraction were tested and a dose response curve for each fraction was generated. The specific activity in units/mg was then interpolated from the dose response curve.

TABLE II

Purification of the liver derived growth inhibitor:

| Fraction: | Total Protein (mg) | Units/mg Protein | Fold Purification | Total Activity | % Recovery |
|---|---|---|---|---|---|
| Initial homogenate | 1280 | 48 | | 61440 | |
| amm. sulfate precipitate | 600 | 71 | 1.48 | 42600 | 69 |
| QAE sepharose pool | 240 | 167 | 3.48 | 40080 | 65 |
| Octyl-agarose pool | 10 | 252 | 5.25 | 2520 | 4 |
| SP-sepharose pool | 1.4 | 556 | 11.58 | 2592 | 4 |
| Gel filtration pool | 0.14 | 5000 | 104.17 | 690 | 1.1 |

Aliquots of active pooled fractions from each purification step were dialyzed and assayed in parallel on the same plting of target cells. Various levels of each fraction were tested so that a dose response for each could be measured. One unit of inhibitory activity is defined as causing the reduction in the number of cells/well in test wells to 30% of that seen in negative control wells. The protein concentration of each fraction was determined using the Coomassie blue dye binding procedure and the specific acitivity was interpolated from the dose response curve.

Figure 3:
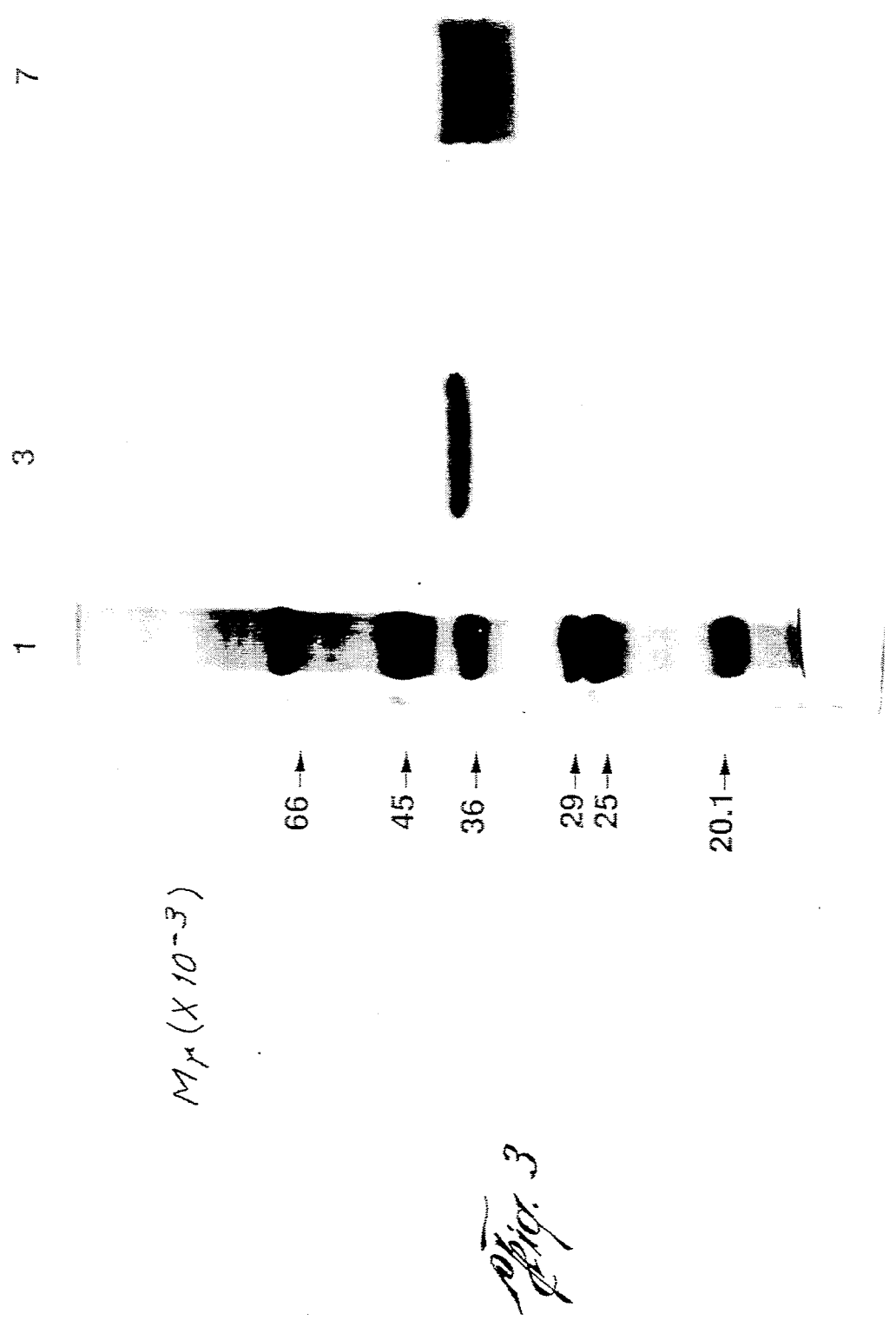

Silver stain analysis of this material following SDS polyacrylamide gel electrophoresis indicated that it consisted of 5–6 very closely running bands of $M_r$ ~38 kD to 40 kD, when reduced (FIG. 3, lane 3), and of 5–6 somewhat more separated bands when not subjected to prior reduction (FIG. 3, lane 7). Exposure of the growth inhibitor from this step to non-reducing Laemmli SDS/PAGE treatment solution at 25° C. followed by extensive dialysis abolished all growth inhibitor activity, making preparative SDS/PAGE unfeasible as a purification step.

EXAMPLE II

CHARACTERIZATION OF THE LIVER-DERIVED TUMOR CELL GROWTH INHIBITOR

A. MATERIALS AND METHODS

1. Preparative iso-electric focusing

An aliquot of active material from the QAE-sepharose step was dialyzed against water containing 10% glycerol. The volume of the dialysate was adjusted to 55 ml and 3 ml of pharmalyte 8.5–10 was added. The sample was introduced into a rotofor apparatus (Bio-Rad, Richmond, Calif.) with recirculating 4° C. coolant and was electrophoresed at 10 w constant power for 4 hours. Fractions were collected and their pH was determined.

2. Exposure to reducing agents

An aliquot of the active material from the gel filtration step was made 10 mM in dithiothreitol (DTT) and incubated at 25° C. for 2 hours. The sample was then dialyzed against 25 mM HEPES, pH 7.5 and assayed against a dialyzed, untreated control.

3. Assay for transforming growth factor beta (TGF-b) activity

The human Moser colon carcinoma cell line is known to be stimulated to produce both fibronectin (FN) and carcinoembryonic antigen (CEA) upon exposure to TGF-b (Chakrabarty et al, 1988). Serum free cultures of Moser were made 10 ng/ml in TGF-b or 10% v/v in liver derived growth inhibitor from the gel filtration step. After a 3 day incubation, both FN (Varani and Chakrabarty, 1990) and CEA (Chakrabarty et al, 1988) were measured in the Moser conditioned tissue culture media by ELISA.

4. Comparative effect of the growth inhibitor on cells RAW117-P and H10: Cells were plated at 10,000 cells/dish in 100 mm petri dishes in 10 ml high glucose, 25 mM HEPES buffered (pH 7.5) DMEM media containing 2% FBS. In test dishes, the media was made 1% v/v in inhibitor from the octyl agarose step. Control dishes received the same amount of inhibitor solvent. On ensuing days, 100 μl of media was withdrawn from the dishes and cell density in that aliquot was determined with a model ZM Coulter Counter.

A375p and A375Li: Cells were plated at 2,000 cells/well in 96 well plates in DME:F12 (1:1, v:v) media containing 2% FBS. One day after plating, increasing levels of liver derived growth inhibitor from the gel filtration step were added in quadruplicate into various wells. Six days later, cell numbers were determined using the crystal violet stain assay.

B. RESULTS

Figure 4:
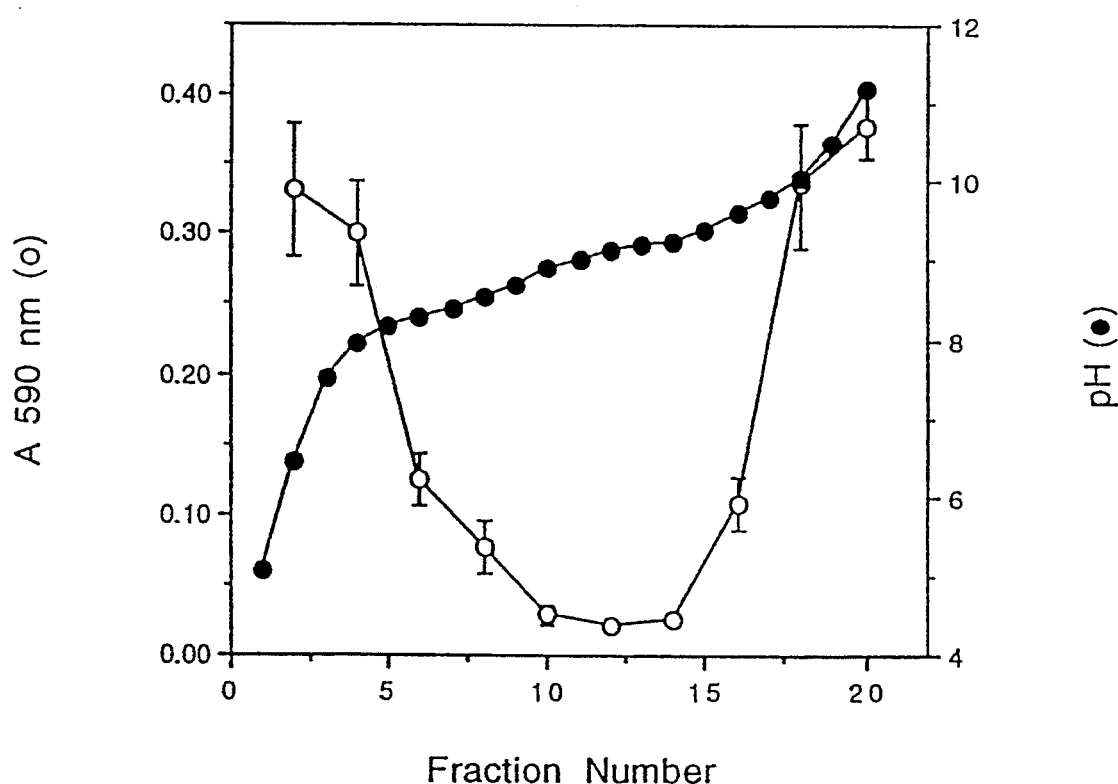
FIG. 4. Separation of the active fraction from the QAE sepharose step by preparative electrophoresis using the Rotofor instrument. Target cells used were A375P, and $A_{590}$ represents cell number. Rotofor fractions were dialyzed against 25 mM HEPES, pH 7.5, added into A375P cultures in 96 well plates (initial plate=2,000 cells/well) at 10% v:v, and the cell number was determined 5 days later. Points, mean±S.D. for four replicates.

Preparative iso-electric focusing of a fraction of the material from the QAE-sepharose step demonstrated that the liver derived growth inhibitor possessed a pI of 9.1–9.2 (FIG. 4). This result agreed with the elution characteristics observed during the QAE-sepharose separation and confirmed the high pI of the inhibitor.

Figure 5:
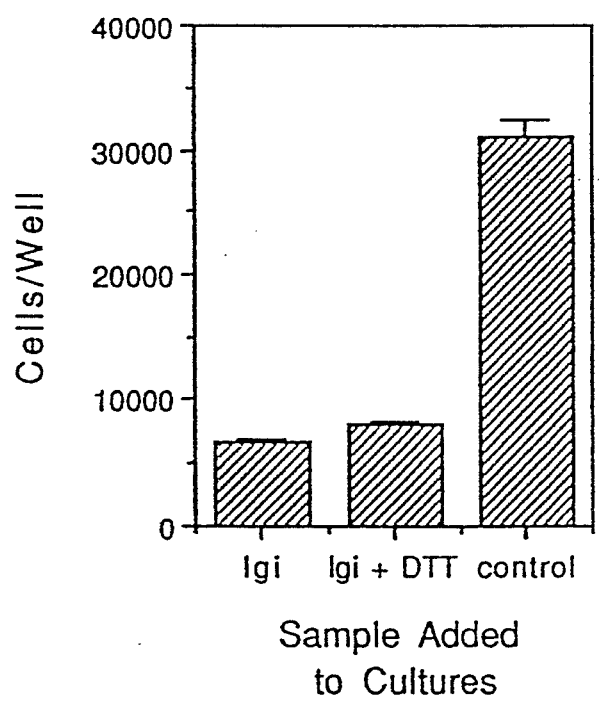
FIG. 5. Effect of dithiothreitol (DTT) treatment of the liver derived growth inhibitor. Material was exposed to 10 mM DTT, dialyzed and tested for its ability to reduce the number of RAW117P cells in media containing 2% fetal bovine serum (FBS) after 5 days in culture. Bars, mean±S.D. for four replicates.

Disruption of intra-chain disulfide bonds had no permanent affect on growth inhibitor activity as exposure of the factor to 10 mM di-thiothreitol caused only a slight and insignificant loss of activity (FIG. 5). Analysis by SDS/PAGE did not indicate any inter-chain disulfide bonds or di-sulfide linked sub-unit structure (FIG. 3).

Figure 6A:
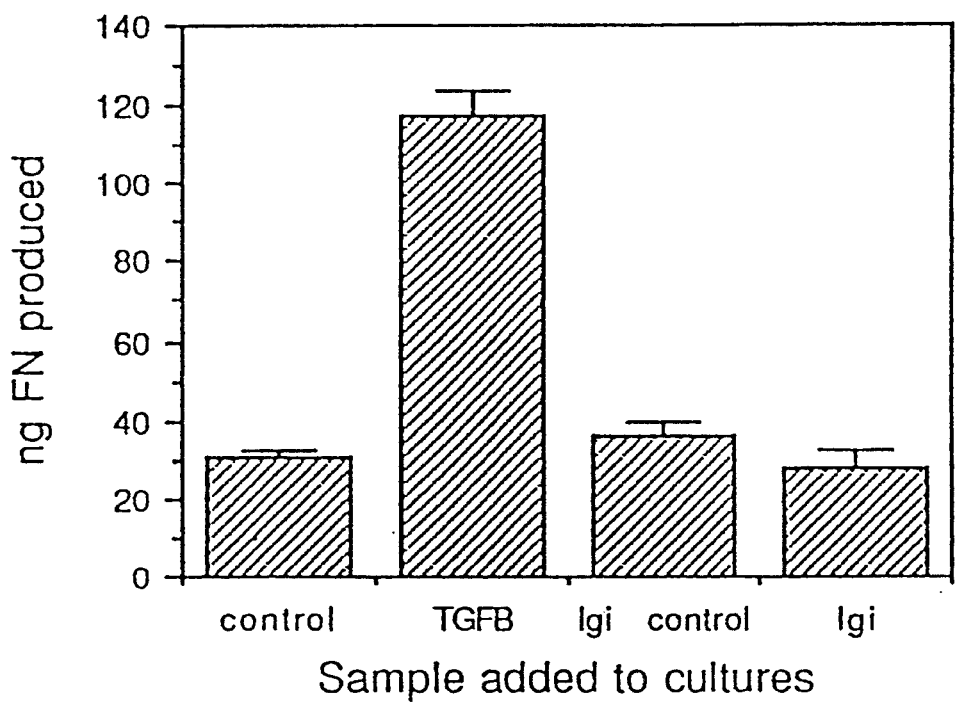
FIGS. 6A and 6B. Comparison of the effects of transforming growth factor beta (TGF-b) and the liver-derived growth inhibitor on the stimulation of fibronectin (FN) and carcinoembryonic antigen (CEA) production by Moser cells. A: ELISA detection of FN in Moser conditioned media; B, ELISA measurement of CEA levels in Moser conditioned media.
Figure 6B:
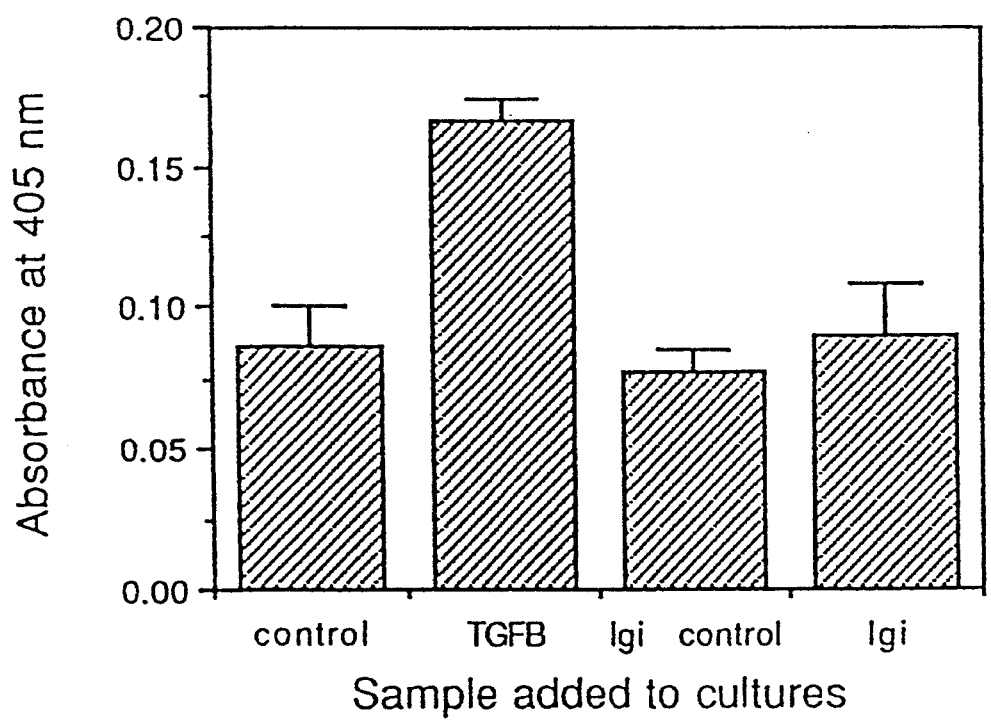

The proliferation inhibitor purified through the gel filtration step possessed no apparent TGF-b activity as assessed by its inability to stimulate fibronectin or carcinoembryonic antigen release by Moser target cells (FIG. 6).

Figure 7A:
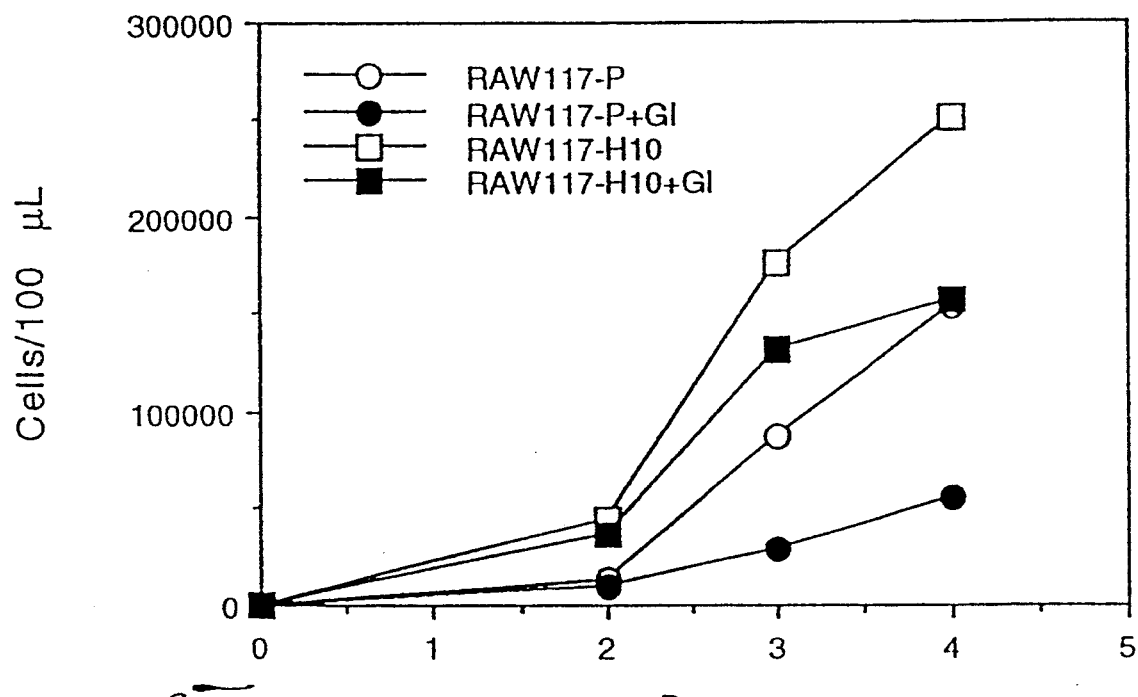
FIGS. 7A and 7B. Differential effects of the liver derived growth inhibitor on liver and non-liver metastasizing lines. A: time course measurement of cell density in RAW117-P and H10 cultures when exposed to the same low levels of liver-derived growth inhibitor or control. Cells were plated at 10,000 cells/dish in 100 mm petri dishes in 10 ml high glucose, 25 mM HEPES buffered (pH 7.5) Dulbeco's modified Eagle's medium (DMEM) containing 2% (FBS). In test dishes, the media was made 1% v/v in inhibitor from the octyl agarose step. Control dishes received the same amount of inhibitor solvent. On ensuing days, 100 µl of media was withdrawn from the dishes and cell density was determined. B: cell quantitation of A375P or Li cells in cultures after five days exposure to increasing levels of liver-derived growth inhibitor. Cells were plated at 2,000 cells/well in 96 well plates in DME:F12 (1:1, v:v) media containing 2% FBS. One day after plating, increasing levels of liver derived growth inhibitor from the gel filtration step were added in quadruplicate into various wells. Six days later, cell numbers were determined using the crystal violet stain assay. Points represent the mean±S.D. for four replicates.
Figure 7B:
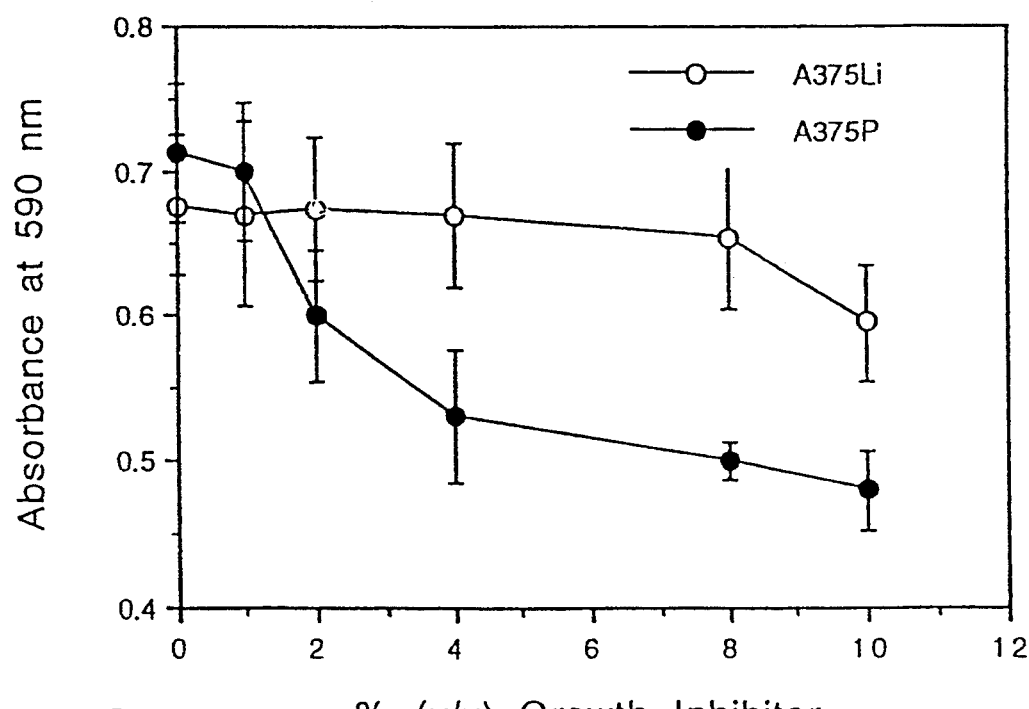

When tested for differential effects on liver versus non-liver metastasizing tumor cell lines, the growth inhibitor displayed a greater potency on the non-liver metastasizing lines in two systems studied. In a time source study using a growth inhibitor dose calculated to be near the $ED_{50}$ for RAW117-P cells, the factor affected the liver metastasizing RAW117-H10 cells to a lesser degree than the non-metastatic RAW117-P (FIG. 7a). In a dose response study using human A375 melanoma cells, the liver metastasizing A375Li was found to be less affected by, and to possess a greater $ED_{50}$ for, the inhibitor than did the non-metastatic A375p cells (FIG. 7b).

The growth inhibitory factor was also observed to inhibit the proliferation of various sublines of the rat 13762NF mammary adenocarcinoma. The non-metastatic MTPa and MTLn2 lines as well as the lung metastasizing MTLn3 line were all affected by the growth inhibitor. With all cell lines examined the growth inhibitor was seen to co-purify; no new major sources of activity from any of the chromatography steps were seen for one cell line and not another.

Procedures performed to assess certain affinity chromatography techniques revealed that the growth inhibitor described here does not adhere to immobilized concanavalin-A or immobilized heparin.

Neither the serum free conditioned media from a rat hepatocyte culture nor a murine hepatic sinusoidal endothelial cell culture were found to exhibit any growth inhibitory activity towards RAW117P cells. If the liver localization of the factor is strictly intracellular, then cell disruption by invading tumor cells might cause the release of small, physiologically relevant amounts of the material.

EXAMPLE III
TREATMENT AND DIAGNOSTIC PROTOCOLS

The growth inhibitor of the present invention has not yet been tested in vivo. However, the in vitro activity of this factor in inhibiting the growth of tumor cells, and particularly, in differentially inhibiting the growth of metastatic and nonmetastatic tumor cells, has been well established herein. This in vitro data is believed to demonstrate the utility of the present invention in regard to a clinical setting in human subjects. The following embodiments are therefore prophetic and represent the methods contemplated by the present inventor for practicing the invention in various clinical settings.

It is believed that the growth inhibitor will prove to be useful in the treatment of various tumors, and in particular, in preventing the metastasis of tumor cells to the liver. The growth inhibitor may be administered by way of direct intravenous infusion within pharmaceutical compositions. Such compositions would include effective doses of the growth inhibitor either alone, or in combination with other therapeutic agents, including perhaps, interleukins, interferon, monoclonal antibodies, antibody toxin conjugates, or indeed, any other therapeutic agent currently used in cancer treatment.

The growth inhibitor could be given daily by continuous infusion or given on alternative days with different therapeutic agents being given on the other day. Doses of the growth inhibitor would be determined by experimental methods, including animals studies and pilot trials with human subjects, each of which are well known to those of skill in the art. One would naturally, as with any new therapeutic agent, conduct a phase I trial to investigate the levels at which any unacceptable toxicity may be reached.

The growth inhibitor of the present invention will additionally be of value as a clinical diagnostic aid to identify tumors which exhibit increased liver-metastasizing potential. As such, it is contemplated that one would obtain cells from a tumor, for example, by performing a tissue biopsy, and then contact the tumor cells with the growth inhibitor. One would then determine the level of cell growth or proliferation, by any of the standard assays employed in the art, in the presence of the inhibitor and compare it to the control growth levels observed in the absence of the inhibitor. Cells observed to exhibit substantial proliferation in the presence of the inhibitor would be identified as cells having increased metastatic potential with respect to the liver. A clinician could then design treatment regimens according to the newly defined properties of the tumor cells.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Brunson, K. W., and Nicolson, G. L. J. Natl. Cancer Inst. 61: 1499–1503 (1978).

Capaldi et al., Biochem. Biophys. Res. Comm. 76:425 (1977).

Chakrabarty, S., Tobon, A., Varani, J., and Brattain, M. G. Cancer Research. 48:4059–4064 (1988).

Chapekar, M. S., Huggett, A. C., and Thorgeirsson, S. S. Experimental Cell Research. 185:247–257 (1989).

Chen, T. S., Ottenweller, J., Luke, A., Santos, S., Keeting, P., Cuy, R., and Lea, M. A. Cytobios 59:79–86 (1989).

Fidler et al. (1976) Cancer Res., 36:3608 (1976).

Huggett, A. C., Krutzcsh, H. C., Thorgeirrson, S. S. J. Cell. Biochemistry. 35: 305–314 (1987).

Kanda, S., Nomata, K., Saha, P. K., Nishimura, N., Yamada, J., Kanetake, H., and Saito, Y. Kidney Int. 37:875–879 (1990).

Keung, W., Silber, E., and Eppenberger, U. Anal. Bioch. 182: 16–19 (1989).

Komatsu, K., Nakamura, H., and Akedo, H. Cell Biol. Int. Reports 10:813–820 (1986).

Laemmli, U.K. Nature (London) 227:680–685 (1970):

McMahon, J. B., Farrelly, J. G., and Iype, T. Proc. Natl. Acad. Sci. USA. 79:456–460 (1982).

Mashima, K. Kimura, T., Huang, W., Yano, K., Ashida, Y., Yamagata, Y., Miyazaki, K., Yamashita, J., and Horio, T. J. Biochemistry. 103: 1020–1026 (1988).

Mayazaki, K., and Horio, T. In Vitro Cellular and Developmental Biology. 25:866–872.

Naito, S., Giavazzi. R., and Fidler, I. J. Invasion and Metastasis. 7:16–29 (1987).

Nicolson, G. L. Expl. Cell Research. 168:572–577 (1987).

Paulsen, J. E., Reichelt, K. L., and Petersen, A. K. Virchows Arch B 54: 152–154 (1987).

Paulsen J. E., Sundby Hall, K., Rugstad, H. E., Reichelt, L., and Elgjo, K. Cancer Research. 52:1218–1221 (1992).

Rosenbaum, J., Mavier, P., Preaux, A., Lescs, M., and Dhumeaux, D. Journal of Hepatology. 9:269–300 (1989).

Reichelt, K. L., Paulsen, J. E., and Elgjo, K. Virchows Arch B 59:137–142 (1990).

Shirasuna, K., Morioka, S., Watatani, K., Hayashido, Y., Furusawa, H., Sugyami, M., Okura, M., and Matsuya, T. Cancer Research 48:2819–2824 (1988).

Sorretino, V. Anticancer Research. 9:1925–1936 (1989).

Varani, J. and Chakrabarty, S J. Cell. Physiology 143:445–454 (1990)

Wu, C., Wang, Y., and Pei, X. Leukemia Research 13:825–831 (1989) .

Wu, C., Pei, X., and Cong, P. Experimental Hematology 17:304–308 (1989a) .

What is claimed is:

1. A purified tumor growth inhibitor having the following properties:
   (a) isolatable from liver cells;
   (b) a molecular weight of approximately 38 kD to 40 kD, as determined by gel filtration chromatography and SDS/PAGE analyses;
   (c) an isoelectric point of approximately 9.1;
   (d) possessing heat stability on exposure to temperatures of from ambient to up to and including 65° C. for a period of time of up to and including one hour; and
   (e) capable of inhibiting murine RAW117 lymphoma cell growth.

2. The growth inhibitor of claim 1, which has been purified between about 1.4–100-fold.

3. The growth inhibitor of claim 2, which has been purified between about 10–100-fold.

4. The growth inhibitor of claim 1, which has been purified about 100-fold.

5. A method of preparing a tumor growth inhibitor, comprising the steps of:
   (a) isolating an extract from liver cells;
   (b) subjecting said extract to fractionation;
   (c) identifying a fraction containing a purified growth inhibitor having the following characteristics:
      i) a molecular weight of approximately 38 kD to 40 kD and an isoelectric point of approximately 9.1 as determined by gel filtrating chromatography and SDS/PAGE analyses;
      ii) possessing heat stability on exposure to temperatures of from ambient to up to including 65 degrees C. for a period of time of up to and including one hour;
      iii) capable of inhibiting murine RAW117 lymphoma cell growth; and
   (d) collecting said fraction.

6. The method of claim 5, wherein step (b) futher comprises subjecting the extract to fractionation by heat treatment, ammonium sulfate precipitation, or chromatography.

7. The method of claim 6, wherein the extract is further fractionated according to charge, hydrophobicity, or size.

8. A purified tumor growth inhibitor, isolatable by the process of claim 5.

9. The growth inhibitor of claim 8, further defined as a growth inhibitor with a molecular weight of approximately 38 kD to 40 kD, an isoelectric point of approximately 9.1, and which is capable of inhibiting murine RAW117 lymphoma cell growth.

10. A pharmaceutical composition of a growth inhibitor comprising the therapeutically effective amount growth inhibitor of claim 1 dispersed in a pharmacologically acceptable vehicle.

11. The pharmaceutical preparation of claim 10, in a form suitable for parenteral administration.

12. A method for inhibiting the metastasis of a tumor to the liver of an animal:
   (a) preparing the tumor growth inhibitor in accordance with claim 1; and
   (b) administering a therapeutically effective amount of said growth inhibitor to an animal with a tumor.

13. A method in accordance with claim 12, wherein the growth inhibitor is administered to the animal parenterally.

14. The method of claim 12, performed subsequent to or simultaneously with surgical removal of the tumor from the animal.

* * * * *

UNITED STATES PATENT AND TRADEMARK OFFICE
CERTIFICATE OF CORRECTION

PATENT NO.   : 5,393,534
DATED        : February 28, 1995
INVENTOR(S)  : Philip G. Cavanaugh and Garth L. Nicolson It is certified that error appears in the above-indentified patent and that said Letters Patent is hereby corrected as shown below:

In claim 5, column 18, line 23, delete "filtrating" and replace with -- filtration --.

In claim 6, column 18, line 31, delete "futher" and replace with -- further --.

Signed and Sealed this

Sixteenth Day of May, 1995

Attest:

BRUCE LEHMAN

*Attesting Officer*    *Commissioner of Patents and Trademarks*